United States Patent [19]

Morel

[11] Patent Number: 4,621,165

[45] Date of Patent: Nov. 4, 1986

[54] PROCESS FOR REMOVING CERTAIN LINEAR ISOPRENE TRIMERS FROM A MIXTURE OF ISOPRENE TRIMERS

[75] Inventor: Didier Morel, Lyons, France

[73] Assignee: Rhone-Poulenc Sante, Courbevoie, France

[21] Appl. No.: 582,908

[22] Filed: Feb. 23, 1984

[30] Foreign Application Priority Data

Feb. 24, 1983 [FR] France .................................. 83 03002

[51] Int. Cl.$^4$ .................................................. C07C 7/00
[52] U.S. Cl. ........................................ 585/866; 585/864; 560/126; 568/395
[58] Field of Search ............... 585/866, 864; 560/126, 560/174; 568/31, 395; 203/38

[56] References Cited

U.S. PATENT DOCUMENTS

| | | | |
|---|---|---|---|
| 2,402,954 | 7/1946 | Francis | 585/866 |
| 2,506,289 | 5/1950 | Beach et al. | 585/866 |
| 3,031,515 | 4/1962 | Deprez | 585/866 |
| 3,998,872 | 12/1976 | Symon | 568/395 |
| 4,460,786 | 7/1984 | Morel | 560/126 |

OTHER PUBLICATIONS

S. Akutagawa et al, "Metal-Assisted Terpenoid Synthesis", Bull. Soc. Chim. Japan, 51, 1158–1162 (1978).

*Primary Examiner*—William R. Dixon, Jr.
*Assistant Examiner*—Cynthia A. Prezlock
*Attorney, Agent, or Firm*—Stevens, Davis, Miller & Mosher

[57] ABSTRACT

A process for removing from a mixture of isoprene trimers compounds of the formula

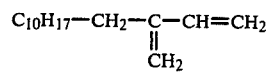

by reacting a mixture of cyclic and linear trimers with a compound having an activated carbon atom, of the formula:

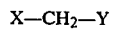

in which one of X or Y is an electron-withdrawing group and the other is an electron-withdrawing or electron-donating group, in the presence of a catalyst consisting of a water-soluble phosphine and a rhodium compound, the reaction being carried out in water or in a water-alcohol medium, and separating the cyclic trimers and linear trimers containing the chain

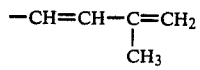

from the mixture of products of the formulae:

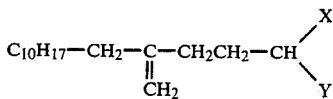

and

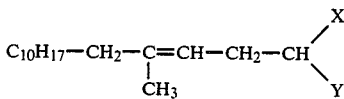

which can be used, in particular, in the synthesis of vitamin E.

14 Claims, No Drawings

PROCESS FOR REMOVING CERTAIN LINEAR ISOPRENE TRIMERS FROM A MIXTURE OF ISOPRENE TRIMERS

The present invention provides a process for removing, from a mixture of isoprene trimers, compounds of the formula:

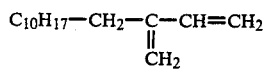
(I)

Trimerisation of isoprene in the presence of a catalyst comprising a nickel salt, such as nickel acetylacetonate, an amine, such as pyridine, and a reducing agent, such as triethyl-aluminium, at 80° C. gives approximately 15% isoprene dimers ($C_{10}$-cut), 65% trimers ($C_{15}$-cut) and 20% heavier products.

The $C_{15}$-cut, which can easily be isolated by distillation, essentially comprises cyclic trimers (trimethylcyclododecatrienes) and linear trimers of the formulae:

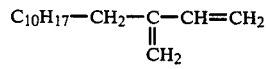
(I)

and

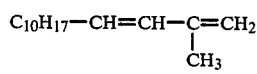
(II)

As an example of a compound of formula (I), β-farnesene is particularly useful as an intermediate in the synthesis of vitamin E via farnesyl-acetone and phytone.

It is known from S. Akutagawa et al, Bull. Soc. Chim. Japan, 51, 1158–1162 (1978) that β-farnesene can be converted into farnesyl-acetone by adding hydrochloric acid in the presence of copper chloride followed by a condensation reaction with methyl acetoacetate in the presence of a strong base, followed by decarboxylation. However, the addition of hydrochloric acid onto 1,3-dienes is not selective, and for example, the addition takes place on both

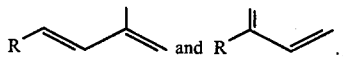

As a result, pure farnesene must be used to carry out the process, in order to obtain farnesyl-acetone having the desired purity.

It is also known, from European Patent Publication No. 44,771, that farnesyl-acetone can be prepared by the reaction of methyl acetoacetate with β-farnesene in the presence of a water-soluble phosphine and a catalyst chosen from inorganic and organic salts and complexes of rhodium, and decarboxylation. However, it is necessary to use purified β-farnesene for selective addition of methyl acetoacetate.

These known processes for the preparation of farnesyl-acetone from β-farnesene thus involve separation of β-farnesene from the $C_{15}$-cut of the isoprene trimers. However, fractional distillation of the $C_{15}$-cut of the isoprene trimers, which contains approximately 45% β-farnesene, does not give a sufficient yield of β-farnesene, since the boiling points of the various trimers are very close, and polymers form on prolonged heating during the course of the distillation.

It has now been found that, amongst the linear isomers contained in the $C_{15}$-cut, only those which have the terminal chain

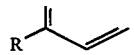

react, under the conditions described in European Patent Publication No. 44,771, with a compound having an activated carbon atom, of the formula:

$$X-CH_2-Y \quad \text{(III)}$$

in which one of X or Y is an electron-withdrawing group and the other is an electron-withdrawing or electron-donating group. Compounds of formula (III) react with the trimers of formula (I) in the $C_{15}$-cut, which has been separated off from the $C_{10}$-cut and heavier products by distillation, without substantially affecting trimers of formula (II) or cyclic trimers.

Reaction of the $C_{15}$-cut with a compound of formula (III) provides compounds of formulae:

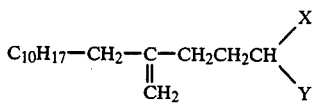
(IV)

and

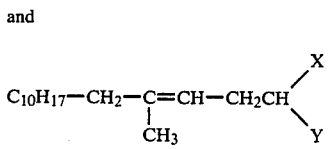
(V)

in which X and Y are as defined above, which are then easily separated from the cyclic trimers and the linear trimers of formula (II) in the mixture, for example by distillation.

According to the present invention, the $C_{15}$-cut is reacted with a compound of formula (III) in the presence of a catalyst comprising a water-soluble phosphine and at least one rhodium compound capable of dissolving in water under the reaction conditions by a coordination reaction with the water soluble phosphine, the reaction being carried out in water or in a water-alcohol mixture containing 0%–50% of an aliphatic alcohol containing 1 to 3 carbon atoms, and the reaction mixture is then fractionated, e.g. by distillation in a manner such that compounds of formulae (IV) and (V) are separated off from the cyclic trimers and the linear trimers of formula (II) and any unreacted linear trimer of formula (I).

Preferably, in compounds of formula (III), one of X or Y is an electron-withdrawing radical of the formulae CHO, $COR_1$, $CO_2R_2$, $SO_2R_3$, $CONR_4R_5$, CN or $NO_2$, and the other is an electron-withdrawing radical as defined above or an electron-donating radical of the formulae $NHCOR_7$, $OR_8$, OH, $OCOR_9$, $SR_{10}$ or SH or a halogen atom, in which $R_1$, $R_2$, $R_3$, $R_4$, $R_5$, $R_7$, $R_8$, $R_9$ and $R_{10}$ are hydrocarbon radicals containing 1 to 12 carbon atoms. If one of the radicals X or Y is an electron-withdrawing group and the other is an electron-donating group, they should be chosen in such a manner that the effect of the electron-withdrawing grouping is predominant.

Examples of compounds of formula (III) are: pentane-2,4-dione $CH_3COCH_2COCH_3$, butan-1-al-3-one $CH_3COCH_2CHO$, ethyl acetoacetate $CH_3COCH_2COOC_2H_5$, methyl acetoacetate $CH_3COCH_2COOCH_3$, phenylsulphonylacetone $C_6H_5SO_2CH_2COCH_3$, ethyl phenylsulphonylacetate $C_6H_5SO_2CH_2CO_2C_2H_5$, ethylsulphonyl-acetone. $C_2H_5SO_2CH_2COCH_3$, $CH_3COCH_2CON(CH_3)_2$, $CH_3COCH_2CON(CH_3)C_2H_5$, ethyl cyanoacetate $NCCH_2CO_2C_2H_5$, cyano-acetone $NCCH_2COCH_3$, ethyl nitroacetate $NO_2CH_2CO_2C_2H_5$, nitro-acetone $NO_2CH_2COCH_3$, diethyl malonate $CH_2(CO_2C_2H_5)_2$ and hydroxy-acetone $HOCH_2COCH_3$. The preferred compounds are methyl acetoacetate and ethyl acetoacetate.

Water-soluble phosphines which may be used are described in French Pat. No. 2,366,237.

Preferably, at least one phosphine of the formula:

                                  (VI)

in which: $Ar_1$, $Ar_2$ and $Ar_3$, which are identical or different, are phenyl or naphthylene radicals, these radicals being unsubstituted or substituted; M is a cationic radical of mineral or organic origin chosen so that the phosphine is water-soluble, and $n_1$, $n_2$ and $n_3$ which are identical or different, are integers from 0 to 3 at least one of them being greater than or equal to 1, is used.

The phenyl and naphthylene radicals may be substituted by any radicals which do not interfere with the water-solubility of the phosphine. Examples of these are alkyl or alkoxy radicals having 1 to 6 carbon atoms, halogen atoms and —OH, —CN, —$NO_2$, —N-(alkyl)$_2$ and carboxylate radicals.

Preferably the phosphine of formula (VI) in which $Ar_1$, $Ar_2$ and $Ar_3$, which are identical or different, contains the substituted or unsubstituted radicals. More preferably, a phosphine in which at least one of the $SO_3M$ groups is in the meta-position of the benzene ring is used.

M is preferably a $Na^+$, $K^+$, $Ca^{++}$, $Ba^{++}$, $NH_4^+$, or quaternary ammonium ion, such as tetramethylammonium, tetrapropylammonium and tetrabutylammonium ions.

$n_1$, $n_2$ and $n_3$ are preferably equal to 0 or 1, $n_1+n_2+n_3$ being from 1 to 3.

Compounds of formula (VI) are more preferably phosphines of the formulae:

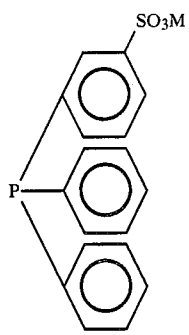

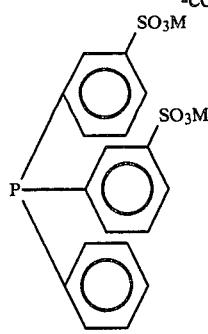

-continued

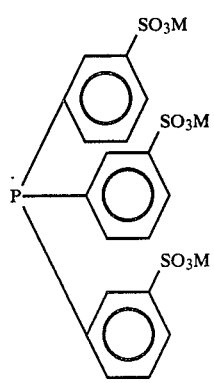

where M has the meaning above.

Examples of the phosphine which can be used in the process according to the invention are: alkali metal, alkaline earth metal, ammonium or quaternary ammonium salts of (p-sulphophenyl)-diphenylphosphine; (m-sulpho-p-methylphenyl)-di-(p-methylphenyl)-phosphine; (m-sulpho-p-methoxyphenyl)-di-(p-methoxyphenyl)-phosphine; (m-sulpho-p-chlorophenyl)-di-(p-chlorophenyl)-phosphine; di-(p-sulphophenyl)-phenyl-phosphine; di-(m-sulpho-p-methylphenyl)-(p-methylphenyl)-phosphine; di-(m-sulpho-p-methoxymethyl)-(p-methoxyphenyl)-phosphine; di-(m-sulpho-p-chlorophenyl)-(p-chlorophenyl)-phosphine; tri-(p-sulphophenyl)-phosphine; tri-(m-sulpho-p-methylphenyl)-phosphine; tri-(m-sulpho-p-methoxyphenyl)-phosphine; tri-(m-sulpho-p-methoxyphenyl)-phosphine; tri-(m-sulpho-p-chlorophenyl)-phosphine; (o-sulpho-p-methylphenyl)-(m-sulpho-p-methyl)-(m,m'-disulpho-p-methyl)-phosphine and (m-sulphophenyl)-(m-sulpho-p-chlorophenyl)-(m,m'-disulpho-p-chlorophenyl)-phosphine.

The rhodium compound used must be water-soluble or capable of dissolving in water under the reaction conditions, by a coordination reaction with the water-soluble phosphines. Preferably the rhodium compound is chosen from the oxides, the inorganic and organic salts and rhodium complexes, for example, $RhCl_3$, $RhBr_3$, $Rh_2O$, $Rh_2O_3$, $Rh(NO_3)_3$, $Rh(CH_3COO)_3$, $Rh(CH_3COCHCOCH_3)_3$, $[RhCl(cycloocta-1,5-diene)]_2$, $[RhCl(CO)_2]_2$ and $RhCl_3(C_2H_5NH_2)_3$.

An amount of rhodium such that the number of gram atoms of elemental rhodium per liter of reaction solution is between $10^{-4}$ and 1 is used.

The amount of phosphine is chosen such that the number of gram atoms of trivalent phosphorus per gram atom of rhodium is between 0.1 and 200.

Although not essential, a reducing agent for rhodium, such as sodium borohydride, zinc powder, potassium borohydride, magnesium or hydrazine, can be added to the reaction mixture.

A base may be added to the reaction mixture to improve the reactivity. Examples of suitable bases are the hydroxides, carbonates and bicarbonates of the alkali metals and alkaline earth metals and tertiary aliphatic or aromatic amines. Between 0.005 and 5 mol of base/liter of aqueous solution are preferably used.

The temperature at which the reaction is carried out can vary within wide limits. Preferably, the reaction is carried out at temperatures below 200° C., more preferably from 50° C. to 125° C.

The minimum amount of water necessary is that sufficient to dissolve all of the catalyst and at least some of the reactants, the reaction taking place in the aqueous phase and the products of the reaction being in the water-immiscible organic phase.

In order to increase the kinetics of the reaction and to facilitate recycling of the catalyst, it is possible to carry out the reaction in the presence of a co-solvent. For example, some of the water required to carry out the reaction may be replaced by an equivalent amount of an aliphatic alcohol containing 1 to 3 carbon atoms, such as methanol, ethanol or isopropanol. The maximum amount of water which may be replaced is half the amount of water necessary for carrying out the reaction without a co-solvent.

A practical way of carrying out the process consists in charging a suitable reactor, which has been purged with an inert gas, for example nitrogen or argon, with either the aqueous or aqueous-alcoholic solution of the catalyst formed beforehand or the various components: phosphine, water, if appropriate alcohol, rhodium compound and, if appropriate a reducing agent and a base. The reactor may be brought to the reaction temperature before or after the introduction of the compound of formula (III), which itself can be introduced before, after or simultaneously with the $C_{15}$-cut to be treated.

When the reaction has stopped, the mixture is cooled to ambient temperature. The contents of the reactor are withdrawn and the reaction product, which is in the organic phase, is isolated by separating the latter from the aqueous phase containing the catalyst by decantation and, if appropriate, by extraction with the aid of a suitable solvent.

The residual aqueous or aqueous-alcoholic solution can be recycled into the reactor to catalyse a new reaction. For example, in aqueous-methanolic solution, the catalyst can be recycled more than 25 times without losing activity. The aqueous or aqueous-alcoholic solution can also remain in the reactor, the organic products then being withdrawn after decantation.

In this process the degree of conversion of trimers of formula (I) is in general greater than 90% and the selectivity is in general greater than 95%.

If methyl acetoacetate is used as the compound of formula (III), the compounds obtained may be decarboxylated and separated, e.g. by distillation, from the trimers which have not reacted. The ethylenic ketones thus obtained can then be hydrogenated, e.g. in the presence of palladium on charcoal, to give the corresponding saturated ketones, for example phytone which is used in the synthesis of vitamin E.

The following examples demonstrate how the invention can be put into practice.

EXAMPLE 1

[RhCl(Cycloocta-1,5-diene)]$_2$ (0.0406 g, 0.105 milligram atom of rhodium),

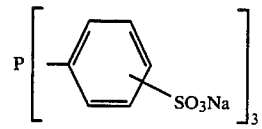

(0.6322 g) (which will be called TPPTS Na in the following examples), equivalent to 0.83 milligram atoms of $P^{3+}$, $Na_2CO_3$ (0.101 g, 0.95 millimole), water (15 cc) and methanol (5 cc) are introduced successively into a stainless steel autoclave which has first been purged with argon. Methyl acetoacetate (10.76 g, 92.8 millimoles) and a $C_{15}$-cut mixture (6.74 g) containing reactants of formula (I) (2.58 g, 12.65 millimoles), olefines of formula (II) (2.7 g, 13.2 millimoles) and trimethylcyclododecatrienes (1.46 g) are then added.

The autoclave is heated at 80° C. for 16 hours, with stirring.

After the aqueous phase containing the catalyst has been separated off by decantation, the organic phase (7.98 g) which is free from methyl acetoacetate but contains reactants of formula (I) (0.26 g), olefins of formula (II) (2.7 g), trimethylcyclododecatrienes (1.46 g) and an equimolar mixture (3.57 g) of products (a) and (a') of formulae:

$$C_{10}H_{17}-CH_2-\underset{\underset{CH_2}{\|}}{C}-CH_2-CH_2-CH\diagup^{COOCH_3}_{\diagdown COCH_3} \quad (a)$$

and $$C_{10}H_{17}-CH_2-\underset{\underset{CH_3}{|}}{C}=CH-CH_2-CH\diagup^{COOCH_3}_{\diagdown COCH_3} \quad (a')$$

is recovered, corresponding to a degree of conversion of formula (I) of 90% and of methyl acetoacetate of 12%; the selectivity for products of formulae (a) and (a') is 98%.

After the mixture of products (a) and (a') has been treated with aqueous sodium hydroxide solution and sulphuric acid, a mixture (2.83 g) of ketones of formulae:

$$C_{10}H_{17}-CH_2-\underset{\underset{CH_3}{|}}{C}=CH-CH_2CH_2-\underset{\underset{O}{\|}}{C}-CH_3 \quad (c')$$

and $$C_{10}H_{17}-CH_2-\underset{\underset{CH_2}{\|}}{C}-CH_2-CH_2-CH_2-\underset{\underset{O}{\|}}{C}-CH_3 \quad (c)$$

and olefins (4.42 g) is obtained.

The $C_{15}$-cut can be prepared in the following manner:

Nickel acetylacetonate (1.28 g, 5 millimoles) in 4% strength solution in toluene, pyridine (15.7 g, 0.2 mole) and isoprene (10 cc, 0.1 mole) are introduced into a 100 cc flask which has first been purged with argon. After the flask has been cooled to −10° C., triethylaluminium (AlEt$_3$) (15 millimoles) in toluene is slowly added. The solution, which is initially blue-turquoise in colour, becomes maroon and then red after heating to 20° C.

This catalytic solution is introduced into a cylindrical stainless steel 125 cc reactor containing isoprene (90 cc, 0.9 mole). The mixture is heated at 80° C. for 8 hours, with stirring.

After cooling, the reaction mixture is poured into 3N hydrochloric acid (100 cc), and pentane (100 cc) is added. After stirring until the mixture has decolorised and the pyridine has dissolved in the water, the reaction mixture is decanted, and the organic layer is concentrated. An organic layer (21.5 g) containing toluene (5.24 g), C$_{10}$-cut (2.45 g) and C$_{15}$-cut (10.61 g), consisting of compounds of formula (I) (4.77 g) and heavier products (3.20 g) (according to analysis by gaseous phase chromatography) is thus obtained.

The C$_{15}$-cut (6.74 g) containing compounds of formula (I) (2.58 g) is obtained by distillation.

EXAMPLE 2

[RhCl(Cycloocta-1,5-diene)]$_2$ (0.0408 g, 0.165 milligram atom of Rh), TPPTS Na (0.613 g, 0.80 milligram atom of P$^{3+}$), Na$_2$CO$_3$ (0.2 g, 1.89 millimoles), water (15 cc) and methanol (5 cc) are introduced successively into a stainless steel autoclave which has first been purged with argon.

Methyl acetoacetate (11.08 g, 95.5 millimoles) and a C$_{15}$-cut (14.46 g), containing reactants of formula (I) (4.9 g, 24 millimoles), olefins of formula (II) (6.66 g, 32.6 millimoles) and trimethylcyclododecatrienes (2.9 g) are then added.

The autoclave is heated at 80° C. for 14 hours, with stirring.

After the aqueous phase containing the catalyst has been separated off by decantation, organic phase (16.6 g) containing reactants of formula (I) (0.78 g), olefins of formula (II) (6.66 g), trimethylcyclododecatrienes (2.9 g) and an equimolar mixture (6.26 g) of products (a) and (a') is recovered, corresponding to a degree of conversion of formula (I) of 84% and of methyl acetoacetate of 20.5%; the selectivity for products of formulae (a) and (a') is 75%.

EXAMPLE 3

[RhCl(Cycloocta-1,5-diene)]$_2$ (0.0504 g, 0.206 milligram atom of Rh), TPPTS Na (0.6 g, 0.96 milligram atom of P$^{3+}$), Na$_2$CO$_3$ (0.101 g, 0.95 millimole), water (15 cc) and methanol (5 cc) are introduced successively into a stainless steel reactor, with central stirring, which has first been purged with argon.

Methyl acetoacetate (16.29 g, 140.43 millimoles) and a C$_{15}$-cut (11.84 g) containing C$_{10}$H$_{16}$ olefins (dimers of isoprene) (1.47 g), reactants of formula (I) (6.45 g, 31.6 millimoles) and olefins of formula (II) and trimethylcyclododecatrienes (4.14 g) are then added.

The reactor is heated at 80° C. for 16 hours, with stirring.

After the aqueous phase containing the catalyst has been separated off by decantation, the concentrated organic phase (14.62 g) containing C$_{10}$H$_{16}$ olefins (1.07 g), reactants of formula (I) (1.25 g), olefins of formula (II), trimethylcyclododecatrienes (4.14 g) and an equimolar mixture (8.16 g) of products (a) and (a') is recovered, corresponding to a degree of conversion of formula (I) of 80.7% and of methyl acetoacetate of 18.1%; the selectivity for products of formulae (a) and (a') is 95%.

The organic phase is then treated with a mixture of methanol (30 cc), water (10 cc) and sodium hydroxide (2 g, 50 millimoles) at 20° C. for 20 hours.

After the methanol has been removed under reduced pressure (100 mm Hg; 13 kPa), a 5% strength aqueous solution of sulphuric acid (60 grams, 30.6 millimoles) is slowly added.

When decarboxylation is complete, the organic phase (13.14 g) containing an equimolar mixture (6.68 g) of the ketones of formulae (c) and (c') is recovered.

This organic phase is then mixed with pentane (40 cc) and the olefinic double bonds are saturated by hydrogenation at 20° C. under a hydrogen pressure of 30 bar in the presence of catalyst (1 g) consisting of 10% strength palladium on charcoal.

A mixture of ketones (6.83 g) of the formula:

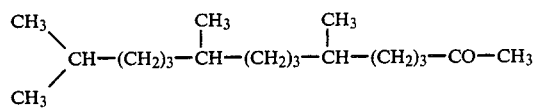

is thus obtained, the $^{13}$C-NMR spectrum of which shows the presence of 50% of phytone of the formula:

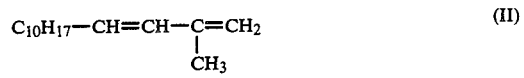

I claim:

1. A process for removing from a mixture of isoprene trimers essentially comprising cyclic trimers and linear trimers of the formulae:

  (I)

and (II)

$C_{10}H_{17}-CH=CH-C=CH_2$
$\phantom{C_{10}H_{17}-CH=CH-}|$
$\phantom{C_{10}H_{17}-CH=CH-}CH_3$ the said trimer of formula (I), which comprises adding to the said mixture a compound having an activated carbon atom, of the formula:

X—CH$_2$—Y  (III)

in which one of X or Y is an electron withdrawing radical of the formulae CHO, COR$_1$, CO$_2$R$_2$, SO$_2$R$_3$, CONR$_4$R$_5$, CN or NO$_2$ and the other is an electron-withdrawing radical as defined above or an electron-donating radical of the formula NHCOR$_7$, OR$_8$, OH, OCOR$_9$, SR$_{10}$ or SH or a halogen atom, in which R$_1$, R$_2$, R$_3$, R$_4$, R$_5$, R$_7$, R$_8$, R$_9$ and R$_{10}$ are hydrocarbon radicals containing 1 to 12 carbon atoms; in the presence of a catalyst comprising (i) a water-soluble phosphine of the formula:

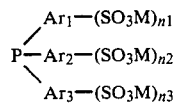

in which $Ar_1$, $Ar_2$ and $Ar_3$, which are identical or different, are phenyl or naphthylene radicals, those radicals being unsubstituted or substituted; M is a cationic radical of mineral or organic origin chosen so that the phosphine is water-soluble, and $n1$, $n2$ and $n3$, which are identical or different, are integers from 0 to 3, at least one of them being greater than or equal to 1; and (ii) at least one rhodium compound, capable of dissolving in water under the reaction conditions by a coordination reaction with the water-soluble phosphine, the amount of rhodium being such as to provide $10^{-4}$ to 1 gram atoms of elemental rhodium per liter of reaction solution and the amount of said phosphine being such as to provide 0.1 to 200 gram atoms of trivalent phosphorus per gram atom of rhodium, in water or a water-alcohol mixture containing 0%–50% of an aliphatic alcohol containing 1 to 3 carbon atoms and in the presence of a base; causing the linear trimers of formula (I) to react at a temperature of 50° to 200° C. with the compound of formula (III) but leaving the cyclic trimers and linear trimers of formula (II) substantially unaffected and separating from the mixture the products of the formulae:

$$C_{10}H_{17}-CH_2-\underset{\underset{CH_2}{\|}}{C}-CH_2CH_2-CH\underset{Y}{\overset{X}{\diagup}} \quad (IV)$$

and $$C_{10}H_{17}-CH_2-\underset{\underset{CH_3}{|}}{C}=CH-CH_2-CH\underset{Y}{\overset{X}{\diagup}} \quad (V)$$

in which X and Y are as defined above.

2. A process according to claim 1, wherein the compound of formula (III) is pentane-2,4-dione, butan-1-al-3-one, ethyl acetoacetate, methyl acetoacetate, phenylsulphonylacetone, ethyl phenylsulphonylacetate, ethylsulphonylacetone, ethyl cyanoacetate, cyano-acetone, ethyl nitro-acetate, nitro-acetone, diethyl malonate or hydroxyacetone.

3. A process according to claim 2, wherein the compound of formula (III) is methyl acetoacetate or ethyl acetoacetate.

4. A process according to claim 1, wherein the phenyl and naphthylene radicals in the water-soluble phosphine are substituted by alkyl or alkoxy radicals having 1 to 6 carbon atoms, halogen atoms, or —OH, —CN, —NO_2, —N-(alkyl)_2 or carboxylate radicals.

5. A process according to claim 1, wherein the phosphine contains substituted or unsubstituted phenyl radicals.

6. A process according to claim 1 wherein the phosphine has at least one of the $SO_3M$ groups in the meta-position of the benzene ring.

7. A process according to claim 1 wherein M in the phosphine is a $Na^+$, $K^+$, $Ca^{++}$, $Ba^{++}$, $NH_4^+$ or quaternary ammonium ion.

8. A process according to claim 7, wherein M is a tetramethylammonium, tetrapropylammonium or a tetrabutylammonium ion.

9. A process according to claim 1 wherein $n1$, $n2$ and $n3$ in the water-soluble phosphine, which may be identical or different, are 0 or 1.

10. A process according to claim 9, wherein the phosphine used has the formula:

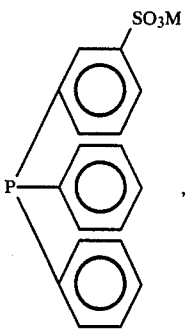

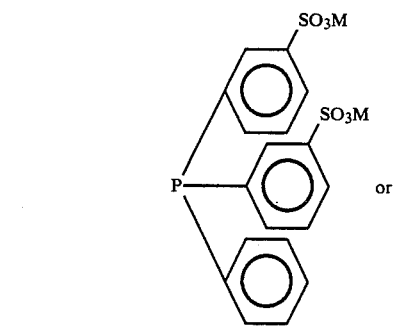

or

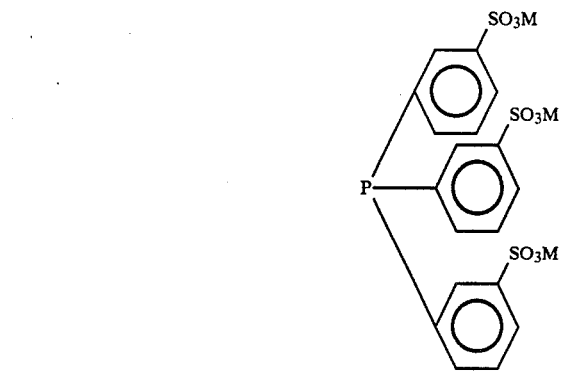

11. A process according to claim 1 wherein the rhodium compound is an oxide, an inorganic or organic salt, or a rhodium complex.

12. A process according to claim 1 wherein the rhodium compound is $RhBr_3$, $Rh_2O$, $Rh_2O_3$, $Rh(NO_3)_3$, $Rh(CH_3COO)_3$, $Rh(CH_3COCHCOCH_3)_3$, $[RhCl(cycloocta-1,5-diene)]_2$, $[RhCl(CO)_2]_2$ or $RhCl_3(C_2H_5NH_2)_3$.

13. A process according to claim 1 wherein a reducing agent for rhodium is added to the reaction mixture.

14. A process according to claim 1 wherein the temperature is from 50° C. to 125° C.